(12) United States Patent
Kofoed et al.

(10) Patent No.: US 6,367,475 B1
(45) Date of Patent: Apr. 9, 2002

(54) RESPIRATORY FLOW METER AND METHODS OF USE

(75) Inventors: Scott A. Kofoed, Bountiful; Kevin Durst, Salt Lake City; Joseph A. Orr, Park City, all of UT (US)

(73) Assignee: Korr Medical Technologies, Inc., Salt Lake City, UT (US)

( * ) Notice: Subject to any disclaimer, the term of this patent is extended or adjusted under 35 U.S.C. 154(b) by 0 days.

(21) Appl. No.: 09/285,129

(22) Filed: Apr. 2, 1999

(51) Int. Cl.⁷ .................................................. A62B 7/00
(52) U.S. Cl. ............................. 128/205.23; 128/200.24
(58) Field of Search .......................... 128/898, 200.14, 128/200.24, 203.23, 204.22, 205.23

(56) References Cited

U.S. PATENT DOCUMENTS

| | | | |
|---|---|---|---|
| 4,296,756 A | 10/1981 | Dunning et al. | |
| 4,731,726 A | 3/1988 | Allen, III | |
| 4,736,750 A | 4/1988 | Valdespino et al. | |
| 4,807,641 A | 2/1989 | Boehringer et al. | |
| 4,975,842 A | 12/1990 | Darrow et al. | |
| 4,991,591 A | 2/1991 | Jones et al. | |
| 5,038,773 A | 8/1991 | Norlien et al. | |
| 5,058,601 A | 10/1991 | Riker | |
| 5,094,246 A * | 3/1992 | Rusz et al. | 600/538 |
| 5,137,026 A | 8/1992 | Waterson et al. | |
| 5,211,180 A * | 5/1993 | Wright et al. | 600/532 |
| D339,635 S | 9/1993 | Waterson et al. | |
| 5,246,010 A | 9/1993 | Gazzara et al. | |
| 5,277,195 A | 1/1994 | Williams | |
| D366,221 S | 1/1996 | Cadera | |
| 5,501,231 A * | 3/1996 | Kaish | 600/532 |
| 5,518,002 A | 5/1996 | Wolf et al. | |
| 5,634,471 A | 6/1997 | Fairfax et al. | |
| 5,724,986 A | 3/1998 | Jones, Jr. et al. | |
| 5,735,287 A | 4/1998 | Thomson | |
| 5,816,246 A | 10/1998 | Mirza | |
| 5,924,994 A * | 7/1999 | Harbrecht et al. | 600/532 |

FOREIGN PATENT DOCUMENTS

GB 2238389 * 5/1991 .................. 600/532

* cited by examiner

Primary Examiner—Glenn K. Dawson
(74) Attorney, Agent, or Firm—TraskBritt (57) ABSTRACT

A peak flow monitoring system having a base unit and a flowhead. The flowhead is designed for roll and snap connection to the base unit so as to be easily removable therefrom after use for ease of cleaning and storage. A gasket compressed between the flowhead and a pressure transducer housed in the base unit forms a pneumatic seal between the two when the flowhead is connected to the base unit, providing a minimal dead volume therebetween. Pressure in the flowhead generated by patient exhalation therethrough is measured by the base unit pressure transducer and a microprocessor computes pulmonary function parameter values from the transducer output for storage and display. The base unit display function includes text-based, customizable, reconfigurable patient symptom and medication queries. Methods of system assembly, disassembly and operation are also disclosed.

19 Claims, 7 Drawing Sheets

RESPIRATORY FLOW METER AND METHODS OF USE

BACKGROUND

1. Field of the Invention

This invention relates to peak respiratory flow monitoring. More specifically, this invention relates to peak flow monitoring of individuals with obstructive respiratory diseases and other conditions and includes apparatus for, and methods of, using this technique in the home and office as well as enhancing patient and physician access to calculated medical data computed therein.

2. Statement of the Art

Peak respiratory flow monitoring of patients with obstructive respiratory diseases or conditions, such as asthma, has been available for many years. Inexpensive mechanical peak flow meters have been used for patient home and office use and many patients have been taught to record their daily peak flow values and their symptoms in a personal diary. The physician then reviews the entries in a patient's diary during regular office visits.

Monitoring of peak respiratory flow helps a patient to manage his or her condition. Generally, peak flow values below 80% of the patient's personal best are an indication that the patient needs more medication or a change in medication to control his or her condition. Peak flow values below 50% of a patient's personal best indicate that the patient should seek medical help immediately.

In measuring and monitoring peak flow, certain pressure data are calculated and evaluated in the form of pulmonary function parameter values. For example, Peak Expiratory Flow (PEF) is the fastest rate at which a person can exhale air out of the lungs after inhaling as large a volume of air as possible. Forced Expiratory Volume (FEVt) is the largest volume of air a person can exhale from the lungs over a time interval, "t." FEV1 is the largest volume of air that a person can exhale from the lungs in one second. Finally, Forced Vital Capacity (FVC) is the largest volume of air a person can exhale from the lungs after a full inspiration, using maximal effort.

Conventional, state-of-the-art equipment used for pulmonary function testing is expensive and requires special training for effective use. Therefore, it is impractical to send pulmonary function testing equipment home with a patient. In response to the perceived need for home monitoring, the aforementioned mechanical peak flow meters were developed to provide a way for the patients to monitor certain elements of respiratory function at home on a daily basis. However, mechanical peak flow meters exhibit substantial deficiencies. Those problems include poor initial accuracy that only worsens as the product ages, difficult-to-read PEF scales that impair reading accuracy, and the inability to integrate gas flow over time to estimate volume related parameters, such as FEV1 or FVC.

Recently, electronic peak flow meters have become available for patient home and office use. These devices typically include the capability to calculate additional parameters associated with a forced vital capacity (FVC) maneuver, such as FEV1. These devices will typically have internal non-volatile memory for storing the PEF and FEV1 results.

Most electronic peak flow meters also provide a red-yellow-green zone respiratory flow indicator. A "green" zone indicates that a peak respiratory flow value is above 80% of a patient's personal best, or predictive, norm. A yellow zone indicates values above 50% and a red zone, values below 50%. Use of these zones facilitates recognition by the patient and physician of the patient's condition to indicate appropriate treatment for the patient.

In addition, some electronic peak flow meters provide a means to enter patient symptoms and/or medication usage. The entered information is stored in the device's memory as a part of data included in an "electronic diary." The means for symptom and medication entry on existing peak flow meters are extremely limited in flexibility and require the patient to remember numbers or symbols associated with different symptoms.

Furthermore, a peak flow meter flowhead which is easily removable and replaceable by a patient is not believed to be present in conventional devices. The flowhead is the tube through which a patient exhales for measuring and monitoring certain peak flow pressure data. The flowhead can become partially occluded from repeated usage, with the device consequently losing its ability to accurately measure the increased pressure created inside the tube during exhalation. Thus, an easily removable flowhead that can also be easily cleaned or stored between readings so as to prevent such loss in accuracy is needed.

Further, conventional electronic peak flow meters employing pressure transducers exhibit an undesirable magnitude of internal volume extending between the aperture or pressure tap opening into the flowhead and the transducer employed to sense pressure generated therein, thus reducing the sensitivity of these devices. In addition, tubing conventionally used to connect the flowhead to the transducer may collect moisture or otherwise become obstructed from the patient's exhalations therein, also impairing operation.

BRIEF SUMMARY OF THE INVENTION

In accordance with the present invention, a peak respiratory flow monitoring system and methods of use are provided for monitoring patients with obstructive respiratory diseases or conditions, such as asthma. The system comprises a microprocessor-equipped base unit and a flowhead connected by a snap-fit therein. The base unit is capable of customizing reconfigurable text-based display messages storable in non-volatile memory and further comprises a pressure transducer housed within the base unit and located immediately adjacent a port in a receptacle on the base unit exterior. The flowhead is designed to be rollingly secured in the receptacle, and secured disposition of the flowhead in the receptacle results in a compression-type pneumatic connection and seal between the flowhead and the pressure transducer of the base unit. When such connection and seal is effected, a pressure generated in the flowhead can be communicated to the pressure transducer within the base unit and corresponding respiratory flow computed by the microprocessor while minimizing internal excess or "dead" system volume by substantially eliminating any significant passage distance between the flowhead and the pressure transducer. The rolling connection and pneumatic seal between the flowhead and the pressure transducer of the base unit is effected by inserting a tab on the flowhead exterior with a corresponding slot in the wall of the receptacle while substantially concurrently rolling the flowhead to align a nipple on the flowhead exterior with the port in the wall of the receptacle and compress a gasket between the nipple and the pressure transducer within the base unit aligned with and immediately adjacent the port.

A method of using the peak flow monitoring system to monitor patients with obstructive respiratory diseases or conditions according to the present invention may be characterized, by way of example, as follows. First, a flowhead is rotatingly connected to a receptacle on the exterior of a base unit while a tap on the flowhead is concurrently operably and directly connected to a pressure transducer housed within the base unit via an intervening gasket surrounding a nipple on the flowhead aligned with a port in the wall of the receptacle. This connection forms a pneumatic seal between the flowhead and pressure transducer with minimal dead volume. Next, a pressure is generated in the flowhead by the patient's respiratory (expiratory) flow therethrough, such pressure being communicated between the nipple and the port and through the gasket to the pressure transducer, the output of which is employed by the microprocessor in computing pulmonary function parameter values. These computed pulmonary function parameter values may then be either displayed as messages on a display, stored in a non-volatile memory, or retrieved and played back from memory using a keypad. Additional information can also be inserted into the base unit using the keypad for display as another display message on the display, stored with other display messages in the non-volatile memory, or retrieved using the keypad. In addition, an interface is provided for reconfiguring the display messages using an external host device such as a personal computer. Finally, the flowhead can be rotatingly disconnected from the receptacle and the base unit for cleaning or storage purposes.

BRIEF DESCRIPTION OF THE DRAWINGS

In the drawings, which illustrate what is currently considered to be the best mode for carrying out the invention.

The present invention will be better understood when the drawing figures are taken in conjunction with the detailed description of the invention set forth hereafter.

DETAILED DESCRIPTION OF THE ILLUSTRATIONS

FIGS. 1–7 of the drawings illustrate the peak flow monitoring system 10 of the present invention including a flowhead 12 and a base unit 14. The base unit 14 may be also referred to as a monitoring device and the flowhead 12 as a pneumotach.

As shown in FIGS. 1, 4, 6 and 7, base unit 14 comprises a display 16, a keypad 18, and non-volatile memory 20. The display is a text-based display and the term "keypad" encompasses a keyboard. The base unit 14 also houses a pressure transducer 22 disposed adjacent to a port 23 in a sidewall of an arcuate receptacle 24 on the exterior of base unit 14. Pressure transducer 22 is operably connected to a microprocessor 25, also housed within the base unit 14, both components being mounted to a printed circuit board 26 as known in the art. The base unit 14 is battery-powered, as shown in FIG. 5.

The flowhead 12 is rollingly, pneumatically connected to the pressure transducer 22 at the receptacle 24, as will be described below. The keypad 18 is used for entering patient information and for accessing the display 16. Keypad functions includes a playback function hereinafter described, and the display 16 is used for displaying retrievable, reconfigurable text-based display messages or display screens 27 comprising calculated data as well as patient information.

Figures 1, 1A:
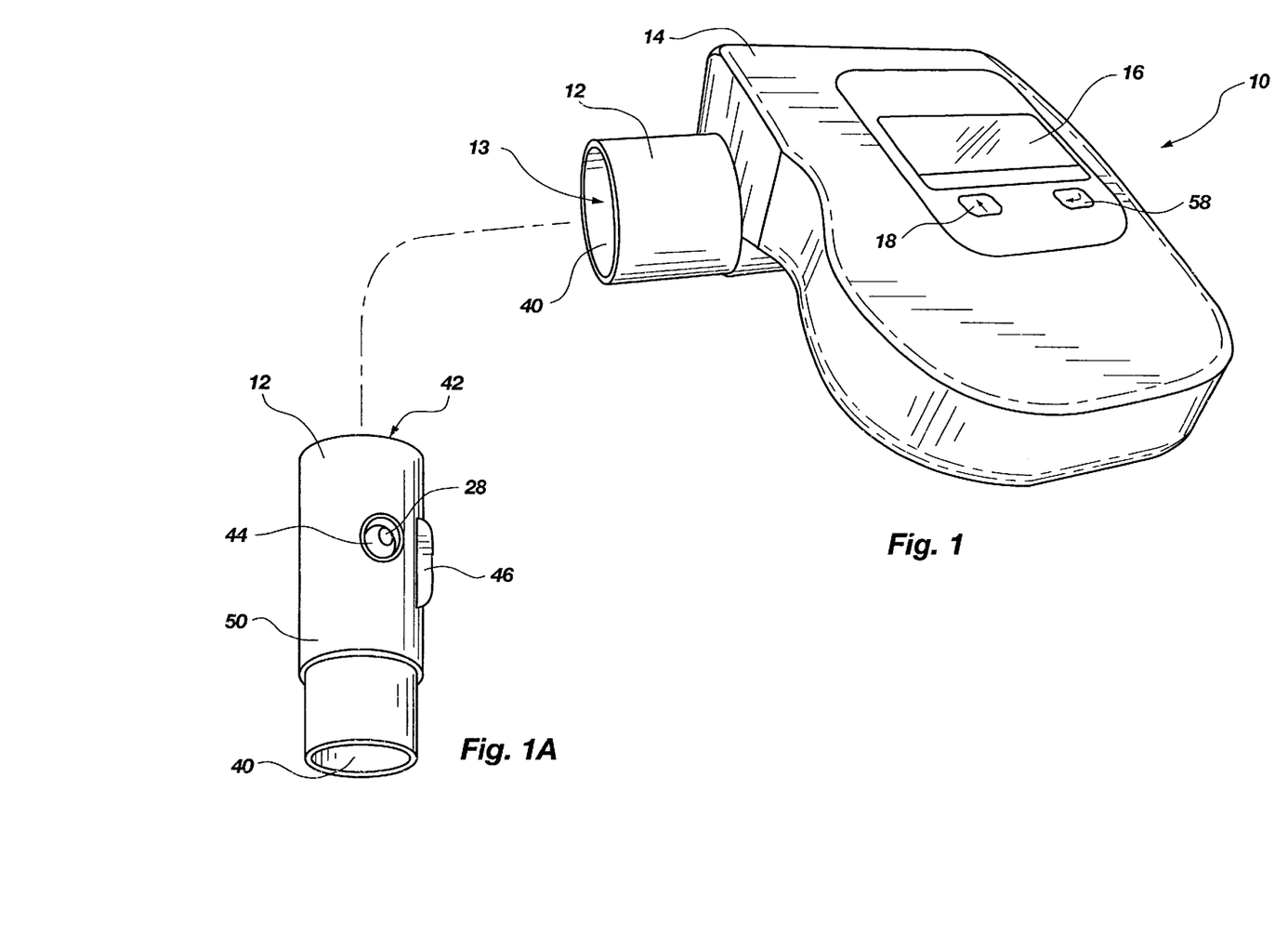
FIG. 1 is a perspective top view of an embodiment of the peak flow monitoring system of the present invention including a base unit having a display and a keypad and a flowhead secured thereto.
FIG. 1A is a perspective top view of the flowhead as removed from the base unit and showing a nipple and a tab on the flowhead exterior.
Figures 2, 3:
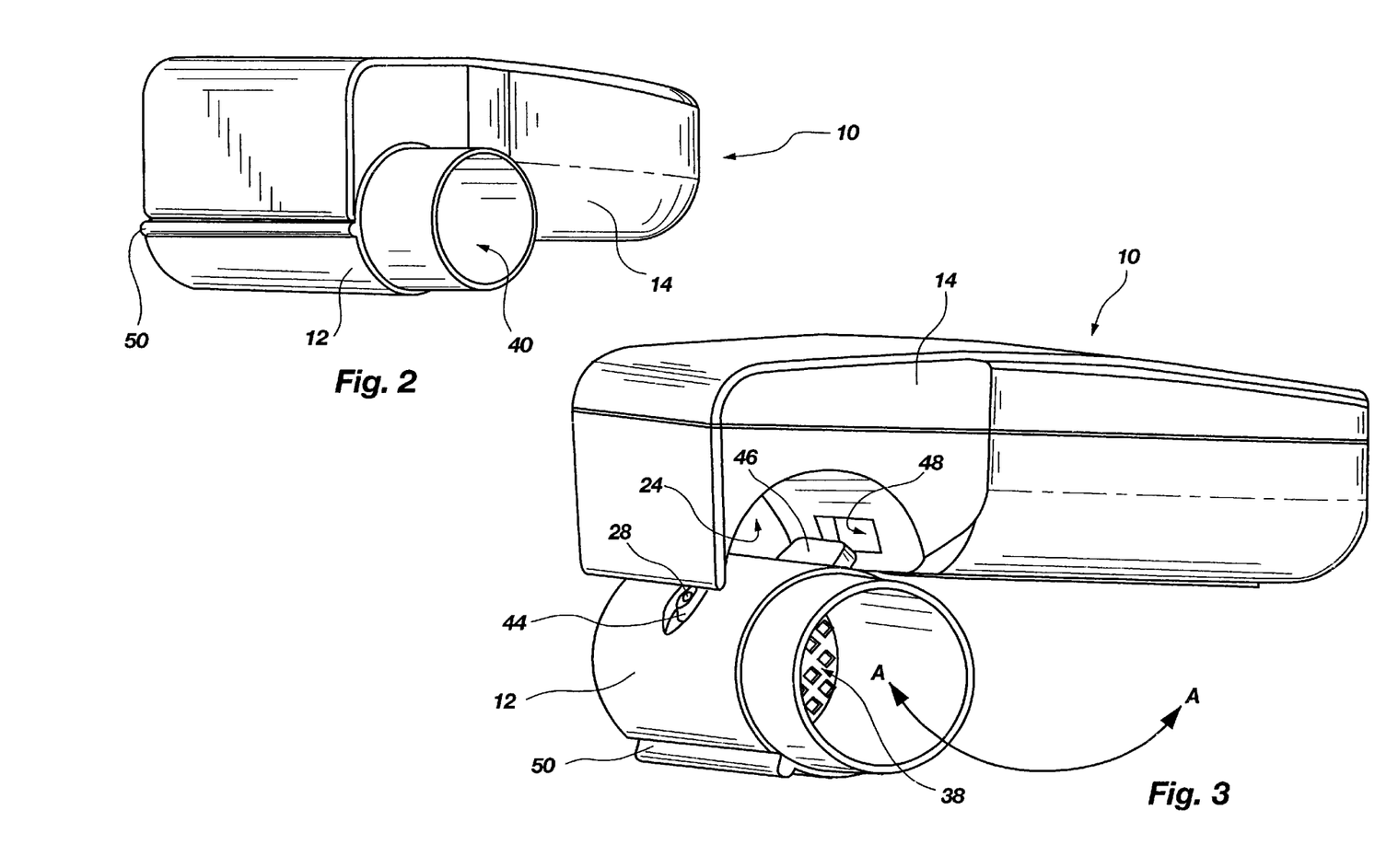
FIG. 2 is a perspective side view of the embodiment of FIG. 1 showing the flowhead in place in the base unit receptacle.
FIG. 3 is a perspective side view of the embodiment of FIG. 1 showing a roll-in and roll-out snap fit connection of the flowhead to the base unit receptacle.
Figure 4:
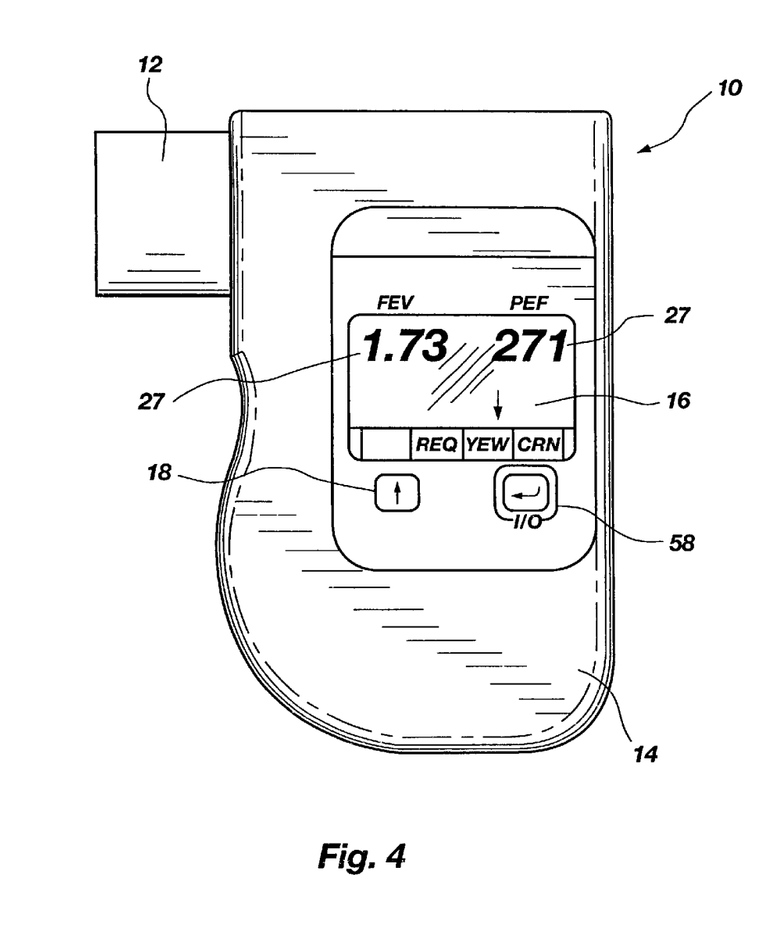
FIG. 4 is a top view of the embodiment of FIG. 1 showing the base unit with display and keypad and a portion of the flowhead extending beyond one side of the base unit.
Figure 5:
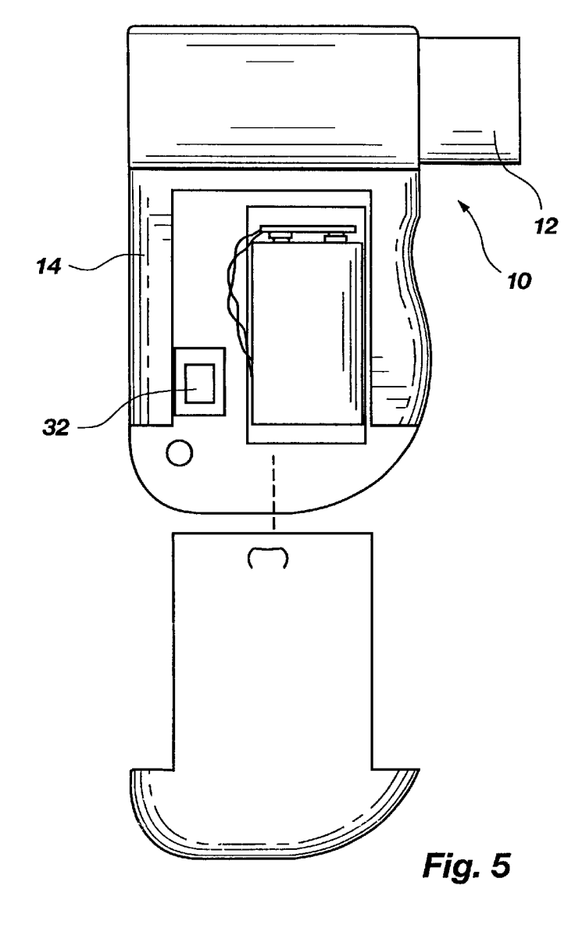
FIG. 5 is a bottom view of the embodiment of FIG. 1 with a cover removed to show a serial communications interface used to communicate with the base unit by a host device and the base unit battery location.
Figure 6:
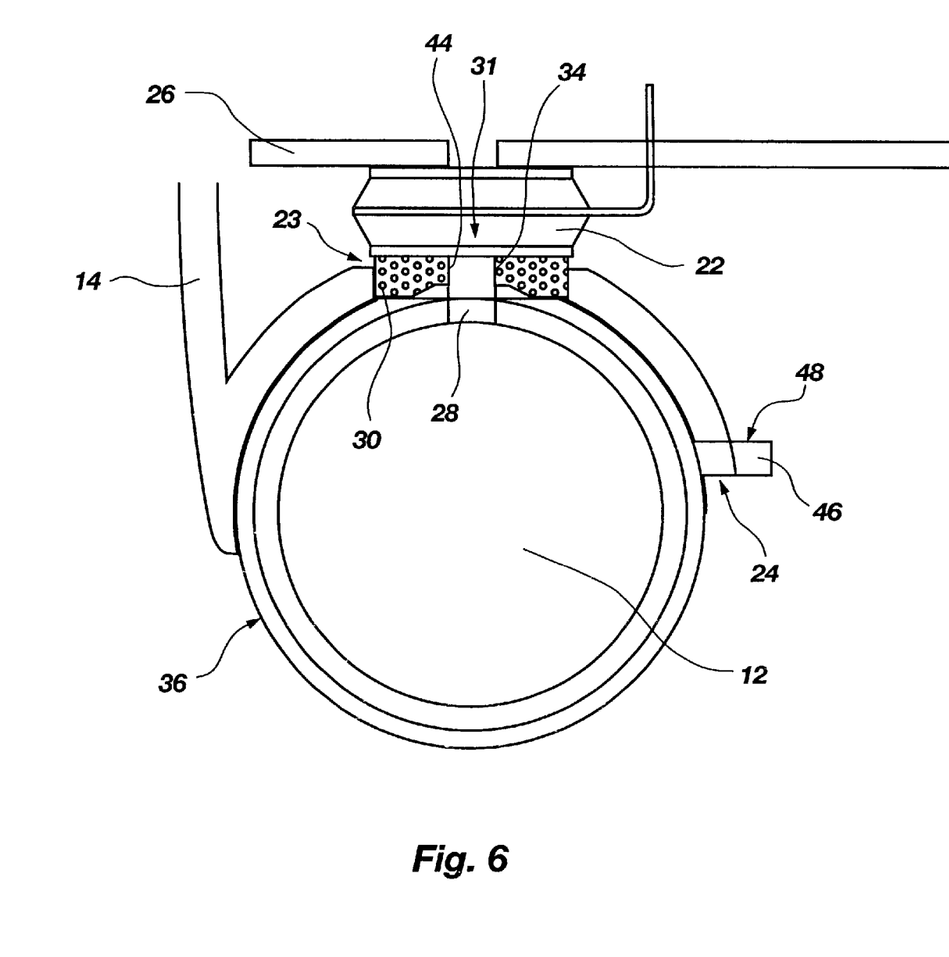
FIG. 6 is a sectional view showing the connection of the flowhead to the receptacle of the base unit including a gasket mounted to the base unit pressure transducer and surrounding the inlet port thereof, compressed between the transducer and the nipple of the flowhead.

The flowhead 12, shown in FIGS. 1–6, is a significant feature of the present invention and is designed for rolling connection to the receptacle 24 and is operably connected directly to pressure transducer 22 without the use of intervening passages to increase system volume. The pressure generated in the flowhead 12 is thus communicated to the pressure transducer 22 in base unit 14 and pulmonary function parameter values computed therefrom for pulmonary monitoring purposes. Specifically, as the patient's exhalation flows through the flowhead 12, a pressure is generated within the flowhead. As shown in FIGS. 3 and 6, the flowhead pressure is then communicated from a tap 28 extending from the flowhead interior to the exterior thereof through a nipple 44 on the flowhead exterior and through an aperture in the center of annular gasket 30 compressed between the flowhead exterior and pressure transducer 22 directly into the pressure transducer 22 located adjacent port 23 in the wall of receptacle 24. An annular, pneumatic seal 34 is formed by compression of the gasket 30 between pressure transducer 22 adjacent the sidewall of receptacle 24 and the exterior of the flowhead 12, thus providing minimal internal dead volume between the flowhead 12 and the pressure transducer 22. This minimal internal dead volume found in region 31, defined essentially as the area between nipple 44 and the face of pressure transducer 22 and bounded by compressed gasket 30, in turn enhances the accuracy and response of the pressure transducer 22 and decreases the adverse effect of any potential gas leaks between the flowhead 12 and pressure transducer 22 by minimizing pressure gradients that would be associated with such leaks. The gasket 30 can be an annular gasket such as an o-ring or other annular elastomeric structure, or any other suitable sealing structure known in the art that would provide the stated pneumatic seal and connection with the desired minimal dead volume. For example, a closed-cell foam gasket of silicon rubber may be employed.

Figure 7:
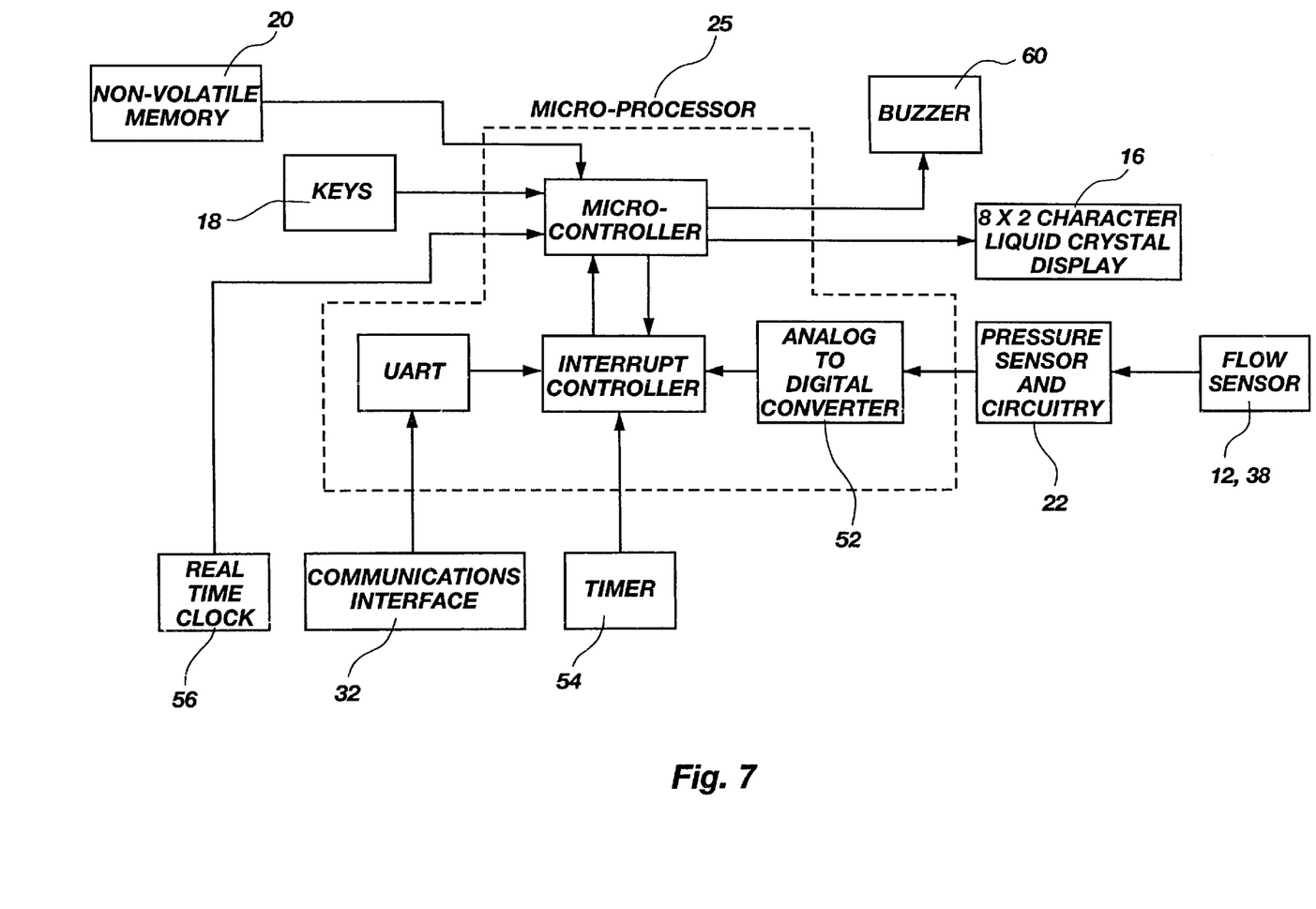
FIG. 7 is a block diagram of major components of the peak flow monitoring system of the invention.

Microprocessor 25, as shown in FIG. 7, is programmed as known in the art to compute pressure, flow rate, and other pulmonary function parameter values, such as FEV1, FVC, and peak forced expiratory flow rate, from the output of pressure transducer 22. Microprocessor 25 may thereafter display the detected pressure as such calculated data on the display 16. The microprocessor 25 may also store the calculated data in the non-volatile memory 20 for subsequent retrieval and display, and is capable of transmitting the calculated data to an external host device such as a personal computer (not shown) external to the system 10 using an electronic communications interface 32. Operation of base unit 14 may be re-configured by, and new display formats for display messages 27 downloaded from, the host device through communications interface 32. As noted, the host device (not shown) may include a personal computer accessed by phone through a modem or directly (onsite) through the communications interface 32 which may comprise an RS232 serial communications interface. However, it is intended that other suitable communications interfaces as known in the art may be employed.

Independent of the measurement of gas flow and the associated parameters, the base unit 14 may be used to record patient symptom and medication data via the keypad 18 and the display 16, as shown in FIGS. 1, and 7. The keypad 18 is operably connected to the display 16. The keypad 18 is configured to enter the patient information, or patient symptom or medication messages, prompted on the display 16 and to subsequently record the patient symptom or medication messages in the non-volatile memory 20 for subsequent reconfiguration, retrieval, and display. The symptoms and/or medications are displayed on the display 16 in order to prompt the patient. The patient can choose between different values for a given symptom or medication, after which the display messages 27 advances to the next symptom and/or medication until all choices have been completed. The patient information is then saved in the non-volatile memory 20 for later retrieval by a physician.

Another significant feature of the base unit 14 of the present invention, as shown in FIGS. 1, 4, 5, 7, and 8, is the capability of customization of the reconfigurable text-based display messages 27. Customization in this context means that a physician may configure or reconfigure the device to the patient's specific needs in terms of symptoms or medication. It is also contemplated that clinical investigators may also configure the device for specific studies wherein the text associated with different symptoms or medications is desirably changed to meet a study protocol. It is not intended that the base unit 14 be limited to these uses only, such uses being merely illustrative of the capabilities of the present invention.

Figure 8:
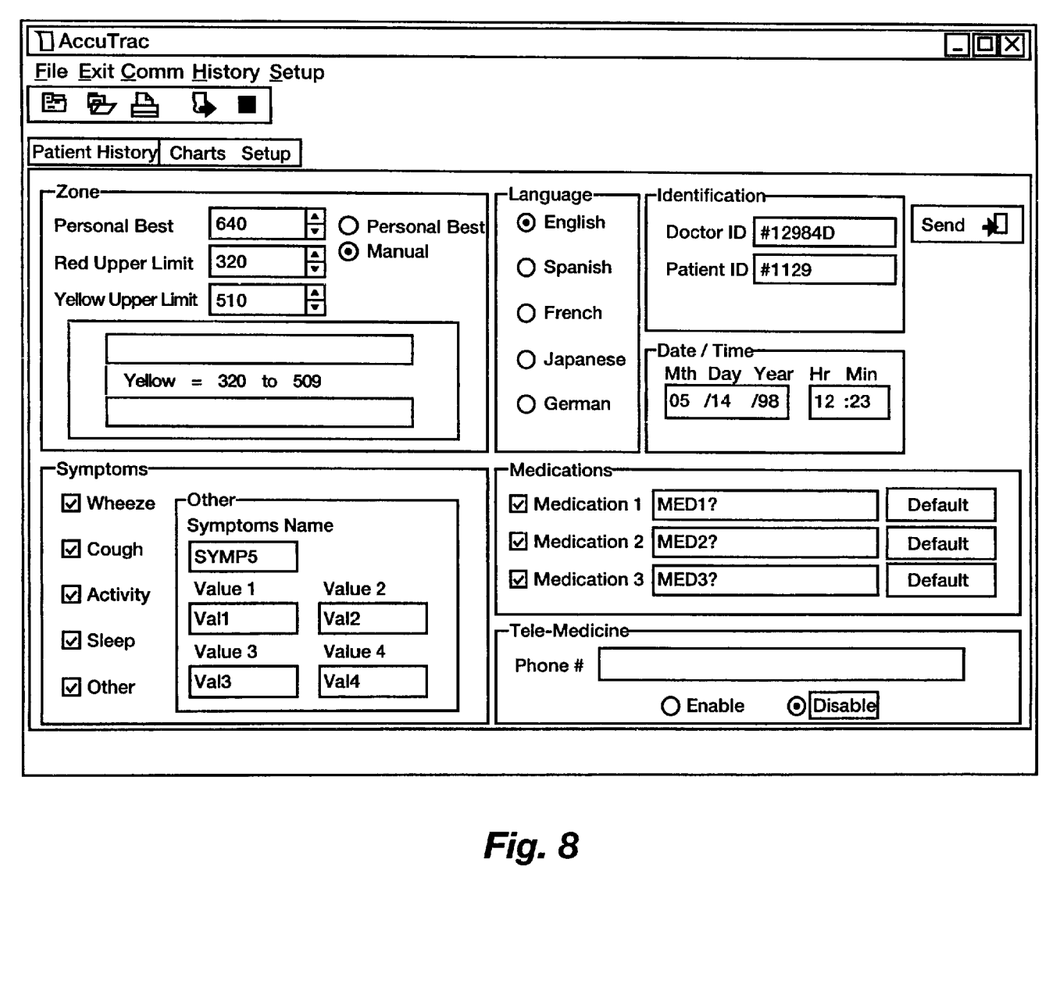
FIG. 8 is a printed computer screen view of the "setup page" of a host device display that a physician uses in the source for message re-configuration of the base unit.

In order to customize the base unit 14, the non-volatile memory 20, or read/write memory, is used to store all display messages 27 as well as the calculated data and the patient information. As described below, the display messages 27 may then be transmitted to the host device (not shown) via the communications interface 32 so that the physician or other authorized individual can then review and, if desired, change the language of the display messages 27 using the host device. In this way, the text associated with the symptom and medication entry portions of the patient information can also be configured as the physician deems necessary for the particular patient and his/her needs. The language of the display messages 27 is reconfigured by downloading new display formats from the host device (not shown) to the base unit 14 through the communications interface 32. FIG. 8 shows an example of a setup page of a host device display screen that the physician would use in order to reconfigure the patient information.

Another significant feature of the present invention is that the base unit 14 is capable of information playback by using the keypad 18, as shown in FIGS. 1, 4, and 7. This means that a patient can retrieve calculated data from the non-volatile memory 20 for personal recordation and pulmonary monitoring purposes. The calculated data offered for subsequent review and separate recording can include PEF, FEV1, and the date for each peak flow maneuver. This allows the patient to record the data into his/her own personal (handwritten) diary (not shown) for the physician's later review. This feature of the present invention also may result in greater patient compliance and discipline in keeping such records and provides a self-management incentive.

The flowhead 12, as shown in FIGS. 1–6, is designed to overcome the problems in the prior art as mentioned above and may be used with peak flow meters using various pressure sensing devices known in the art. The flowhead 12 is designed for roll and snap connection to the base unit 14 as shown at A—A in FIG. 3. This connection technique is significant because it assists the flowhead 12 in forming the compression-type pneumatic seal 34 with the pressure transducer 22 of base unit 14 when removably connected to the base unit 14 so as to direct the flowhead-generated pressure to the pressure transducer 22 for measurement, subsequent computation of pulmonary values therefrom by microprocessor 25, and display. This roll-in design also allows the patient to remove the flowhead 12 for cleaning or storage with relative ease.

As noted previously, this roll-in design with snap fit provides a good pneumatic connection and minimizes gas leaks between the flowhead 12 and the pressure transducer 22. The direct connection of the flowhead 12 to the pressure transducer 22 through the relatively soft, compressed gasket 30 therebetween also minimizes the distance between the flowhead and the pressure transducer (see region 31 in FIG. 6) and eliminates the requirement for connecting tubing such as is employed in the prior art to transmit pressure from a flowhead to a transducer.

As shown in FIGS. 1–3 and 6, the pneumotach or flowhead 12 comprises a peripheral surface 36 and the pressure tap 28, and has a first open end 40 and a second open end 42 located opposite the first open end 40. The peripheral surface 36, or outside surface, extends between the first and second open ends 40, 42, defining a bore 13 through flowhead 12. The pressure tap 28 is located between the first and second open ends 40, 42. In one flowhead embodiment, a grating 38 within bore 13 forms an obstruction to the introduced air flow and causes an increased pressure inside the flowhead 12 proportional to expiratory flow. The first open end 40 receives air flow from the patient while the second open end 42 is open to the atmosphere. The nipple 44 surrounding the pressure tap 28 is located along the peripheral surface 36 for the rolling connection of the flowhead 12 and the pressure transducer 22.

In order to properly align and retain the flowhead 12 inside the receptacle 24 and to effect and maintain the pneumatic seal 34, a tab 46 extends outwardly from the peripheral surface 36, as shown in FIGS. 3 and 6, and extends radially or outwardly so that it engages a slot 48 in the receptacle 24 when the pneumotach 12 is rolled clockwise (as shown in FIG. 3) into engagement, as depicted by arrow A—A, with the receptacle 24. The slot 48 is sized and configured for receiving the tab 46, and the tab 46 and the slot 48 coact, in essence providing a fulcrum by which the flowhead 12 with the base unit 14 may be aligned in to effect the roll-in and roll-out snap fit therebetween, again as depicted by arrow A—A. An outer ridge 50 is also located on the flowhead exterior and is axially oriented so as to facilitate alignment of the flowhead 12 with the base unit 14 as the flowhead 12 is rolled and snapped into receptacle 24.

It is noted that the materials used to construct the base unit, the flowhead, and so forth are to include those materials known in the art and used by the skilled artisan, except as specifically stated otherwise.

Methods of assembling the flowhead 12 with, and disassembling flowhead 12 from, base unit 14 are illustrated in FIGS. 1, 1A, 3 and 6 of the drawings. Methods of using the peak flow monitoring system 10 are depicted in FIGS. 1, 4, 5, and 7–9.

The method of assembly comprises the following acts. First, the flowhead tab 46 is partially inserted into receptacle slot 48 and flowhead 12 is clockwise (as shown in FIG. 3) rollingly inserted into the receptacle 24 of the base unit 14 using ridge 50 as a stop so as to operably align tap 28 with the pressure transducer 22 housed within the base unit 14 with gasket 30 compressed between tap 28 and pressure transducer 22. After use, the flowhead 12 can also be rollingly disassembled from the base unit 14 for cleaning and storage, again as shown by arrow A—A, by rollingly counterclockwise removing the flowhead 12 from receptacle 24 to displace nipple 44 and the tap 28 away from gasket 30 and pressure transducer 22 and then removing the tab 46 from the corresponding slot 48 in the receptacle 24. The disconnected flowhead 12 is then pulled away from the receptacle 24 and the base unit 14.

In operation of system 10, pressure is generated by patient exhalation through the flowhead 12, the pressure being communicated through the tap 28 directly to the pressure transducer 22. This pressure is then processed using the microprocessor 25 and pulmonary function values are computed by programmed microprocessor 25 from the output of pressure transducer 22. These computed pulmonary function values are then displayed on the display 16 and stored in the non-volatile memory 20. Additional patient information such as symptoms or medication taken can also be entered using the keypad 18 and then subsequently displayed on the display 16 and recorded in the non-volatile memory 20. The stored computed pulmonary function parameter values or the stored additional patient information may be reviewed at any time using the keypad 18 and the display 16. Additionally, a host can be interfaced with the base unit 14 to reconfigure the display messages 27 using the interfaced host.

Furthermore, the generated pressure is processed by amplifying and offset adjusting an electrical signal output from the pressure transducer 22 received through an analog-to-digital (A/D) converter 52 included in the microprocessor 25, as shown in FIG. 7. Base unit 14 also includes a timer 54 and clock 56 for data calculation and calendaring purposes as known in the art. A buzzer or other alarm 60 may also be employed to generate audible signals associated with data entry and display.

The display messages 27 may be reconfigured or customized by initially transmitting the stored computed pulmonary function parameter values or the stored additional patient information to the interfaced host device (not shown) for retrieval and analysis. The physician or other clinician may then determine any necessary specific medical needs and accordingly change language or text of the display messages 27 to reflect those needs by selecting new text screens and re-transmitting the selected, changed language or text from the interfaced host device (not shown) back to the base unit 14 for subsequent usage and display.

Figure 9:
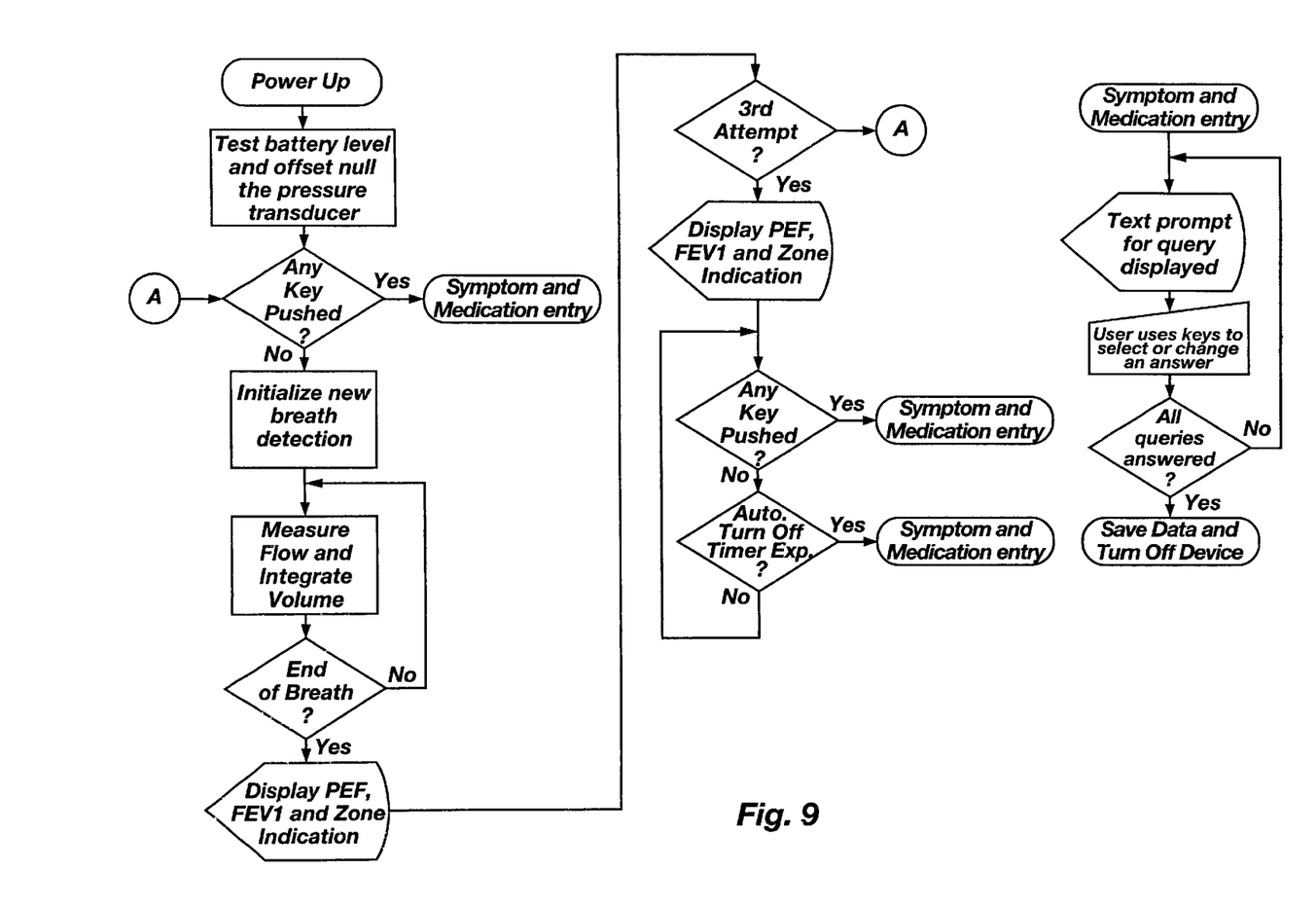
FIG. 9 is a flow chart of system operation options for the patient.

Furthermore, the computed pulmonary function parameter values can be reviewed by a patient at any time for recordation and personal pulmonary maintenance purposes by using the keypad 18 and the display 16. In addition, to record patient information the patient activates the base unit 14 by depressing I/O (On/Off) key 58 on the keypad 18. After the base unit battery level is automatically tested and pressure transducer offset nulled, depression of keypad 18 brings up a symptom and medication entry screen on the display 16 after which the patient can choose and enter values corresponding to a symptom or medication query prompt displayed on the entry screen by again using the keypad 18. The entry screen then advances to the next symptom or medication query prompt and the process repeated until all requested symptoms or medications are entered. If keypad 18 is not depressed or after all queries are answered, base unit 14 is initialized for new breath detection. Respiratory flow is measured and exhaled volume integrated by microprocessor 25 from the output of pressure transducer 22 until the end of a breath is detected (from pressure drop within flowhead 12), at which point PEF and FEV1 are displayed and a ZONE color indicated (see FIG. 4). Three attempts to successfully measure peak flow are permitted by the base unit programming. System 10 may be turned off manually by depressing I/O key 58, saving input and calculated data, or the system automatically turns off to save the battery after a predetermined period of time. A flow chart of possible, exemplary operating sequences of system 10 is illustrated in FIG. 9 of the drawings.

Reference herein to specific details of the illustrated embodiment of the invention is by way of example and not by way of limitation. It will be apparent to those skilled in the art that many additions, deletions and modifications to the illustrated embodiment of the invention may be made without departing from the spirit and scope of the invention as defined by the following claims.

What is claimed is:

1. A peak respiratory flow monitoring system, comprising:
a base unit enclosing a pressure transducer disposed adjacent a port extending through a sidewall of a receptacle on an exterior surface of the base unit; and
a flowhead defining a bore therethrough and having at least an exterior portion configured for receipt within the receptacle so as to effect a pneumatic seal defining communication between the flowhead bore and the pressure transducer through a sidewall of the flowhead.

2. The system of claim 1, wherein the exterior flowhead portion is of arcuate configuration and includes the sidewall of the flowhead.

3. The system of claim 1, wherein said flowhead and said receptacle further include cooperatively-configured structures for mutual engagement so as to promote a roll-in snap fit connection of the flowhead with the receptacle.

4. The system of claim 3, wherein said flowhead further comprises a nipple located on an arcuate exterior portion thereof and the base unit further includes a gasket disposed on the pressure transducer and adjacent the port, the nipple and the gasket being aligned to effect the pneumatic seal when the flowhead arcuate exterior portion is received in the receptacle.

5. The system of claim 4, wherein the gasket comprises an elastomeric annular gasket surrounding and at least partially within the port and effecting the pneumatic seal when compressed by the nipple.

6. The system of claim 5, wherein the cooperatively-configured structures include a tab protruding from the arcuate exterior portion of the flowhead and a slot in the receptacle sidewall sized for receiving the tab.

7. The system of claim 1, wherein the base unit is adapted for receipt of reconfigurable text-based display messages storable in non-volatile memory from a host device through an electronic communications interface.

8. The system of claim 7, wherein the base unit further comprises a microprocessor for computing pulmonary parameter values from an output of the pressure transducer, for initiating display of the computed pulmonary parameter values in a text-based display, for storing the computed pulmonary parameter values in the non-volatile memory for subsequent retrieval, reconfiguration, or display, and for facilitating transmission of the computed pulmonary parameter values to the host device external to said peak flow monitoring system through the communications interface.

9. The system of claim 8, wherein the base unit further comprises a keypad operably connected to a display adapted for displaying the reconfigurable text-based display messages, the keypad being structured for entry of patient symptom or medication values responsive to display of the reconfigurable text-based display messages for recordation thereof in the non-volatile memory for subsequent retrieval or display, the patient symptom or medication values being retrievable from the non-volatile memory by the host device through said communications interface.

10. The system of claim 9, wherein said computed pulmonary parameter values are retrievable from the non-volatile memory using the keypad.

11. A method of using a peak flow monitoring system, comprising:
   generating a pressure in a flowhead responsive to exhalation;
   communicating the generated pressure to a pressure transducer;
   outputting a signal from the pressure transducer responsive to the generated pressure;
   computing at least one pulmonary function parameter value using the signal;
   storing the at least one computed pulmonary function parameter value in non-volatile memory;
   manually inputting additional patient information responsive to reconfigurable display messages;
   storing the manually input additional patient information in the non-volatile memory; and
   reconfiguring at least one reconfigurable display message using an interfaced host device.

12. The method of claim 11, wherein reconfiguring the at least one display message further comprises transmitting the stored computed pulmonary function parameter values or the stored additional patient information to an external interfaced host device, retrieving and analyzing the transmitted stored computed pulmonary function parameter values or stored additional patient information, determining any specific medical requirements, reconfiguring at least one display message to reflect the determined specific medical requirements and transmitting the at least one reconfigured display message from the interfaced host device to the system.

13. The method of claim 11, further comprising activating the system by depressing a key of an input device, initiating a symptom entry message or a medication entry message on a display, and choosing and entering a value corresponding to a symptom or medication displayed with the input device.

14. The method of claim 13, further comprising advancing the display to a subsequent symptom or medication entry message, and entering another value corresponding to a symptom or medication displayed with the input device.

15. The method of claim 11, wherein reconfiguring the at least one reconfigurable display message comprises reconfiguring a text-based message.

16. The method of claim 11, further comprising displaying the at least one computed pulmonary function parameter.

17. The method of claim 11, further comprising displaying the manually input additional patient information.

18. The method of claim 11, further comprising displaying the at least one computed pulmonary function parameter or the manually input additional patient information in response to manual initiation.

19. The method of claim 11, further comprising interfacing the system with an external host device through an electronic communications interface.

* * * * *

UNITED STATES PATENT AND TRADEMARK OFFICE
CERTIFICATE OF CORRECTION

PATENT NO. : 6,367,475 B1
DATED : April 9, 2002
INVENTOR(S) : Scott A. Kofoed, Kevin Durst and Joseph A. Orr It is certified that error appears in the above-identified patent and that said Letters Patent is hereby corrected as shown below:

<u>Column 5,</u>
Line 21, change "1, and 7." to -- 1, 4, and 7. --

Signed and Sealed this

Seventeenth Day of June, 2003

JAMES E. ROGAN
*Director of the United States Patent and Trademark Office*